(12) United States Patent
Sampas (10) Patent No.: US 7,979,215 B2
(45) Date of Patent: Jul. 12, 2011

US007979215B2

(54) METHODS AND SYSTEMS FOR EVALUATING CGH CANDIDATE PROBE NUCLEIC ACID SEQUENCES

(75) Inventor: Nicholas M. Sampas, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 509 days.

(21) Appl. No.: 11/888,038

(22) Filed: Jul. 30, 2007

(65) Prior Publication Data

US 2009/0035764 A1    Feb. 5, 2009

(51) Int. Cl.
*G06F 7/00*    (2006.01)

(52) U.S. Cl. .............. 702/19; 702/20; 703/11; 707/700

(58) Field of Classification Search .................. None
See application file for complete search history.

(56) References Cited

U.S. PATENT DOCUMENTS

| 2004/0191813 A1 | 9/2004 | Bruh et al. |
| 2004/0241658 A1 | 12/2004 | Barrett et al. |
| 2006/0110744 A1* | 5/2006 | Sampas et al. ............... 435/6 |
| 2007/0048743 A1 | 3/2007 | Sampas et al. |

OTHER PUBLICATIONS

Yu et al. Development of a comparative genomic hybridization microarray and demonstration of its utility with 25 well characterized 1p36 deletions; Human Molecular Genetics, 2003, vol. 12, No. 17 pp. 2145-2152.*
Lafrate et al., "Detection of large-scale variation in the human genome", Nature Genetics, vol. 36, No. 9 (Sep. 2004), pp. 949-951.
Tuzun et al., "Fine-scale structural variatio of the human genome", Nature Genetics Advanced Online Publication, (May 15, 2005), http://nature.com/naturegenetics, pp. 1-6.
Feuk et al., "Structural variation in the human genome", Nature Reviews/Genetics, vol. 7, (Feb. 2006), pp. 85-97.

* cited by examiner

*Primary Examiner* — Mary K Zeman
(74) *Attorney, Agent, or Firm* — James S. Keddie; Shweta H. Chandra; Bret E. Field (57) ABSTRACT

Methods of evaluating candidate CGH probe nucleic acid sequences are provided. Aspects of the methods include providing a candidate CGH probe nucleic acid sequence for a target sequence of a copy number variation (CNV) of a genome. A proximity score is then determined for the candidate CGH probe nucleic acid sequence and employed to evaluate the sequence. Aspects of the invention further include computer programming and systems that include the same which are configured to evaluate candidate CGH probe nucleic acid sequences using a proximity score.

18 Claims, 2 Drawing Sheets

METHODS AND SYSTEMS FOR EVALUATING CGH CANDIDATE PROBE NUCLEIC ACID SEQUENCES

INTRODUCTION

Many genomic and genetic studies are directed to the identification of differences in gene dosage or expression among between individuals or cohorts for the study and detection of disease. One class of such differences is referred to in the art as copy number variation. Copy Number Variations (CNV's) are duplications and deletions of genomic material that vary between individuals.

Comparative Genomic Hybridization (CGH) is one approach that has been employed to study genomic variations. In one implementation of CGH, genomic DNA is isolated from normal reference cells, as well as from test cells (e.g., tumor cells). The two nucleic acids are differentially labeled and then simultaneously hybridized in situ to metaphase chromosomes of a reference cell. Chromosomal regions in the test cells which are at increased or decreased copy number relative to the reference cells can be identified by detecting regions where the ratio of the signals from the two distinguishably labeled nucleic acids is altered. For example, those regions that have been decreased in copy number in the test cells will show relatively lower signal from the test nucleic acids than the reference compared to other regions of the genome. Regions that have been increased in copy number in the test cells will show relatively higher signal from the test nucleic acid.

In a recent variation of the above traditional CGH approach, the immobilized chromosome elements have been replaced with a collection of solid support surface-bound polynucleotides, e.g., an array of BAC (bacterial artificial chromosome) clones or cDNAs. Such approaches offer benefits over immobilized chromosome approaches, including a higher resolution, as defined by the ability of the assay to localize chromosomal alterations to specific areas of the genome. However, BACs are typically over 100,000 bp long and the majority of CNVs are smaller than the resolution offer by BAC technologies. Also BACs cannot readily target precisely defined regions as easily as polynucleotide probes.

SUMMARY

Methods of evaluating candidate CGH probe nucleic acid sequences are provided. Aspects of the methods include providing a candidate CGH probe nucleic acid sequence for a target sequence of a copy number variation (CNV) of a genome. A proximity score is then determined for the candidate CGH probe nucleic acid sequence and employed to evaluate the sequence. Aspects of the invention further include computer programming and systems that include the same which are configured to evaluate candidate CGH probe nucleic acid sequences using a proximity score.

DEFINITIONS

The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length, or longer, e.g., up to 500 nt in length or longer. However, in representative embodiments, oligonucleotides are synthetic and, in certain embodiments, are under 50 nucleotides in length.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other nucleic acids that are C-glycosides of a purine or pyrimidine base, polypeptides (proteins), polysaccharides (starches, or polysugars), and other chemical entities that contain repeating units of like chemical structure.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The phrase "labeled population of nucleic acids" refers to mixture of nucleic acids that are detectably labeled, e.g., fluorescently labeled, such that the presence of the nucleic acids can be detected by assessing the presence of the label. A labeled population of nucleic acids is "made from" a chromosome composition, the chromosome composition is usually employed as template for making the population of nucleic acids.

The phrase "surface-bound polynucleotide" refers to a polynucleotide that is immobilized on a surface of a solid substrate, where the substrate can have a variety of configurations, e.g., a sheet, bead, or other structure. In certain embodiments, the collections of polynucleotide probe elements employed herein are present on a surface of the same planar support, e.g., in the form of an array.

The term "array" encompasses the term "microarray" and refers to an ordered array presented for binding to nucleic acids and the like.

An "array," includes any two-dimensional or substantially two-dimensional (as well as a three-dimensional) arrangement of spatially addressable regions bearing nucleic acids, particularly oligonucleotides or synthetic mimetics thereof, and the like. Where the arrays are arrays of nucleic acids, the nucleic acids may be adsorbed physisorbed, chemisorbed, or covalently attached to the arrays at any point or points along the nucleic acid chain.

Any given substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more than ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100μ$^2$, or even smaller. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse-jets of either nucleic acid precursor units (such as monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

An array is "addressable" when it has multiple regions of different moieties (e.g., different oligonucleotide sequences) such that a region (i.e., a "feature" or "spot" of the array) at a particular predetermined location (i.e., an "address") on the array will detect a particular sequence. Array features are typically, but need not be, separated by intervening spaces. In the case of an array in the context of the present application, the "population of labeled nucleic acids" will be referenced as a moiety in a mobile phase (typically fluid), to be detected by "surface-bound polynucleotides" which are bound to the substrate at the various regions. These phrases are synonymous with the terms "target" and "probe", or "probe" and "target", respectively, as they are used in other publications.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as signals (e.g., electrical, optical, radio signals, etc.) over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in array,. Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions determines whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA, or the like.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not especially distinct. In other words, a mixture is not addressable. To be specific, an array of surface bound polynucleotides, as is commonly known in the art and described below, is not a mixture of capture agents because the species of surface bound polynucleotides are spatially distinct and the array is addressable.

"Isolated" or "purified" generally refers to isolation of a substance (compound, polynucleotide, protein, polypeptide, polypeptide, chromosome, etc.) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well known in the art and include, for example, ion-exchange chromatography, affinity chromatography, flow sorting, and sedimentation according to density.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

The term "using" has its conventional application, and, as such, means employing, e.g. putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

"Contacting" means to bring or put together. As such, a first item is contacted with a second item when the two items are brought or put together, e.g., by touching them to each other.

A "probe" means a polynucleotide which can specifically hybridize to a target polynucleotide, either in solution or as a surface-bound polynucleotide.

The term "validated probe" means a probe that has been passed by at least one screening or filtering process in which experimental data related to the performance of the probes was used as part of the selection criteria.

"In silico" means those parameters that can be determined without the need to perform any experiments, by using information either calculated de novo or available from public or private databases.

"Empirical" refers to experimental protocols that include a physical transformation of matter, such as hybridization assays in which an array is contacted with a sample.

The term "genome" refers to all nucleic acid sequences (coding and non-coding) and elements present in or originating from any virus, single cell (prokaryote and eukaryote) or each cell type and their organelles (e.g. mitochondria) in a metazoan organism. The term genome also applies to any naturally occurring or induced variation of these sequences that may be present in a mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism.

For example, the human genome consists of approximately $3 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence.

By "genomic source" is meant the initial nucleic acids that are used as the original nucleic acid source from which the solution phase nucleic acids are produced, e.g., as a template in the labeled solution phase nucleic acid generation protocols described in greater detail below.

The genomic source may be prepared using any convenient protocol. In many embodiments, the genomic source is prepared by first obtaining a starting composition of genomic DNA, e.g., a nuclear fraction of a cell lysate, where any convenient means for obtaining such a fraction may be employed and numerous protocols for doing so are well known in the art. The genomic source is, in many embodiments of interest, genomic DNA representing the entire genome from a particular organism, tissue or cell type. However, in certain embodiments, the genomic source may comprise a portion of the genome, e.g., one or more specific chromosomes or regions thereof, such as PCR amplified regions produced with a pairs of specific primers.

A given initial genomic source may be prepared from a subject, for example a plant or an animal, which subject is suspected of being homozygous or heterozygous for a deletion or amplification of a genomic region. In certain embodiments, the average size of the constituent molecules that make up the initial genomic source typically have an average size of at least about 1 Mb, where a representative range of sizes is from about 50 to about 250 Mb or more, while in other embodiments, the sizes may not exceed about 1 Mb, such that they may be about 1 Mb or smaller, e.g., less than about 500 Kb, etc.

In certain embodiments, the genomic source is "mammalian", where this term is used broadly to describe organisms which are within the class mammalia, including the orders carnivore (e.g., dogs and cats), rodentia (e.g., mice, guinea pigs, and rats), and primates (e.g., humans, chimpanzees, and monkeys), where of particular interest in certain embodiments are human or mouse genomic sources. In certain embodiments, a set of nucleic acid sequences within the genomic source is complex, as the genome contains at least about $1 \times 10^8$ base pairs, including at least about $1 \times 10^9$ base pairs, e.g., about $3 \times 10^9$ base pairs.

Where desired, the initial genomic source may be fragmented in the generation protocol, as desired, to produce a fragmented genomic source, where the molecules have a desired average size range, e.g., up to about 10 Kb, such as up to about 1 Kb, where fragmentation may be achieved using any convenient protocol, including but not limited to: mechanical protocols, e.g., sonication, shearing, etc., chemical protocols, e.g., enzyme digestion, etc.

Where desired, the initial genomic source may be amplified as part of the solution phase nucleic acid generation protocol, where the amplification may or may not occur prior to any fragmentation step. In those embodiments where the produced collection of nucleic acids has substantially the same complexity as the initial genomic source from which it is prepared, the amplification step employed is one that does not reduce the complexity, e.g., one that employs a set of random primers, as described below. For example, the initial genomic source may first be amplified in a manner that results in an amplified version of virtually the whole genome, if not the whole genome, before labeling, where the fragmentation, if employed, may be performed pre- or post-amplification.

DETAILED DESCRIPTION

Methods of evaluating candidate CGH probe nucleic acid sequences are provided. Aspects of the methods include providing a candidate CGH probe nucleic acid sequence for a target sequence that may or may not have an association with any known copy number variation (CNV) of a genome. A proximity score is then determined for the candidate CGH probe nucleic acid sequence and employed to evaluate the sequence. Aspects of the invention further include computer programming and systems that include the same which are configured to evaluate candidate CGH probe nucleic acid sequences using a proximity score.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present invention provides methods of evaluating candidate CGH probe nucleic acid sequences. The phrase candidate CGH probe nucleic acid sequence refers to a sequence of nucleotide residues that has been initially identified as a potential nucleic acid sequence that may be present in physical probe nucleic acid (e.g., where the sequence is the sequence of the entire physical probe or a portion thereof, e.g., 50% or more, such as 75% or more including 90% or more in terms of residue number) that could be used in a comparative genomic hybridization assay. In certain embodiments, the candidate CGH probe nucleic acid sequence is provided in text format or as a string of text, where the text represents or corresponds to the sequence of nucleotides of the nucleic acid. The nucleic acid sequence can be of any length, e.g., from 15 to 250 nt, such as from 15 to 100 nt, and including from 20 nt to about 60 nt in length. However, nucleic acid sequences of lesser or greater length may be used as appropriate.

The methods of evaluating candidate probe nucleic acid sequences may be viewed as in silico methods, where the term in silico is used as defined above. The methods find use in methods of screening candidate sequences for use in physical probes, e.g., in the form of surface-bound polynucleotides, with binding characteristics that make them suitable for use in array-based comparative genome hybridization (aCGH) methods. Accordingly, the invention provides a method of in silico screening in which binding of a candidate surface-bound polynucleotide having a candidate sequence of interest is assessed using the methods described above, and candidate sequences with at least predicted desirable binding characteristics are identified. By providing a method of assessing candidate sequences for use in surface-bound polynucleotides, sequences of polynucleotides predicted to have desirable binding characteristics may be readily identified.

Embodiments of the invention are particularly useful with comparative genome hybridization microarrays, such as microarrays based on the human or mouse genome. Such embodiments permit more cost-effective and efficient identification of gene regions or sections which can be associated with human disease, points of therapeutic intervention, and potential toxic side-effects of proposed therapeutic entities.

In general terms, aspects of the methods for probe selection and validation of the invention comprise, identifying probe properties that can be determined a priori by the probe's sequence and the sequence of the genome it is contained within, and may further comprise expanding the set of properties from those that can be determined a priori, to those that can be measured empirically through simple experiments, such as self-self experiments. The methods of the invention may further comprise measuring the response of candidate probes to a known stimulus, where the stimulus is generated by a set of samples of where the copy numbers for relatively small subsets of the genome are altered in known ways.

Aspects of the invention include providing one or more candidate CGH probe nucleic acid sequences for a target sequence of interest of a copy number variation (CNV) of interest of a genome (or region thereof, e.g., chromosome or chromosomal segment). The one or more candidate CGH probe nucleic acid sequences may be provided using any convenient protocol. An example of a suitable protocol is disclosed in published United States Patent Application No. 20060110744 titled: "Probe design methods and microarrays for comparative genomic hybridization and location analysis," the disclosure of which is herein incorporated by reference.

In certain embodiments, candidate probe sequences are initially identified by selecting sequences that comprehensively cover a whole genome (e.g. the human genome), where the entire genomic sequence is searched when generating specific candidate probes. Such methods may include a homology search. In certain embodiments, known highly repetitive sequences can be removed by a process called RepeatMasking. Repeat-masked genomic sequences are publicly available on the web (e.g. UCSC's website having an address produced by placing "www." before "genomebrowser.org"). Another approach is to reduce the number of probe sequences being searched up-front. This can be done on the basis of any known property of the probe, from thermodynamic properties, such as duplex-Tm and hairpin free energy, to position on the genome. Candidate probe sequences may be selected in terms of "real estate" (number of probes) that is available for a final array that will include the probes. As such, sequence selection may include consideration of the amount of probes or "real estate" to use for specified regulatory regions, intergenic regions as well the amount of probes necessary to adequately cover introns and exons of the chromosomes of interest.

The number of initial candidate probes that is generate may vary considerably. In certain embodiments the number is at least 10, at least 100, at least 1000, at least 10,000, at least 100,000, at least 1,000,000 or more, where in certain embodiments, 20 to 40 million candidate probe sequences may be initially present. In certain embodiments, the candidate sequences have been selected (i.e., designed) according to one or more particular parameters to be suitable for use in a given application, where representative parameters include, but are not limited to: length, melting temperature (Tm), non-homology with other regions of the genome, hybridization signal intensities, kinetic properties under hybridization conditions, etc., see e.g., U.S. Pat. No. 6,251,588, and Published United Sates Application No. 20040002070; the disclosures of which are herein incorporated by reference.

Once the one or more candidate sequences have been provided, e.g., using the probe design protocols as summarized above, a proximity score is determined for the one or more candidate sequences. A proximity score is a function of similarity measures of the candidate CGH probe nucleic sequence for all regions of said genome of interest (or portion thereof) having a sequence that is homologous to the given candidate CGH probe nucleic acid.

Accordingly, one component of determining a proximity score is to identify all regions of a genome (or portion thereof) that having a homology with the candidate probe nucleic acid sequence that is above a given threshold value. In this step, the target genomic loci will be identified, where additional non-target regions may also be identified, e.g., depending the uniqueness of the candidate sequence in the genome of interest, etc. Homology of the candidate sequence may be determined using any convenient protocol, such as but not limited to the BLAST, BLAT or ProbeSpec protocols that find all similar or identical sequences within the genome to any given sequence of interest, such as the probe sequence. Published United States Patent Application No. 20060110744 provides additional details on suitable protocols, the disclosure of which details is herein incorporated by reference. While the homology threshold may vary in a given application, where the Blast protocol is employed using the manufacturer's recommend settings is employed, the homology threshold may be to allow a limited number of hits at fewer than 10, fewer than 20 or fewer than 100 with more than 60% homology, or greater than 50% homology. The above step identifies all regions in the genome (or region thereof that have a homology to the candidate probe sequence that is above a given threshold value of interest, where these regions may be referred to as homologous regions or "hits."

Once the homologous regions or "hits" have been identified, the next step is to determine a proximity score for the probe based the distribution of the hits in the genome. In embodiments where the interval boundaries of the CNV of interest are known, e.g., as determined from the published literature or by direct observations, one can treat near-hits (those homologous genomic sequences nearly identical to the probe or its complement) that lie within the interval as contributing to the "signal" and those that are elsewhere in the genome as contributing to the "background". For example, if a given probe nucleic acid sequence has 3 hits within a CNV having defined interval boundaries and 1 hit outside of these boundaries, a determination is made that one has 3 signal hits and 1 background hit. A ratio of signal to background can then be determined equal to 3. The ratio can then be employed as a proximity score for a given candidate sequence, and employed to evaluate the candidate probe sequence. For example, if this ratio is greater than 1, such as greater than 2, it can be viewed as a good sequence to include in a physical nucleic acid probe molecule.

In certain embodiments, more complicated calculations are employed to determine a proximity score for a given candidate sequence. In certain embodiments, the proximity score is determined from an estimate (D) of signal contributions from distal hybridization events (i.e., distal hits) occurring at genomic regions distal to the target sequence for which the candidate sequence was designed (i.e., the target loci). A given hit may be considered a distal hit if its distance (in terms of nucleotide bases) from the target loci is 5 kbp or more, such as 10 kbp or more and including 40 kbp or more. An example of such an embodiments is where the proximity score is determined using the formula:

$$\text{Proximity score} = 1/(1+D).$$

In certain embodiments, the proximity score is determined from an estimate (D) of signal contributions from distal hybridization events (i.e., distal hits) occurring at genomic regions distal to the target sequence and also from an estimate (P) of signal contributions from proximal hybridization events (i.e., proximal hits) occurring at least proximal to said target sequence. A given hit may be considered a proximal hit if its distance (in terms of nucleotide bases) from the target loci is 20 kbp or less, such as 10 kbp or less and including 5 kb or less. Proximal hits may include the target sequence for which the candidate sequence was designed, as well as one or more additional sequences that are proximal to the target sequence. An example of such an embodiments is where the proximity score is determined using the formula: Proximity score=P/(P+D).

In certain embodiments where a CNV of interest is well characterized, a proximal hit is considered to be one that is within the boundaries of the same known common variation (s) as the probe itself, whereas a hit is considered distal if it is outside all know variations that contain the same probe locus.

Estimates P and D that are employed in determining proximity scores according to embodiments of the invention, e.g., as described above, are made using "effective hit" values and a proximity weighting function. These terms and how they are employed in determining estimates P and D are now reviewed in greater detail.

An "effective hit" ($H_i$) is a normalized ratio of the estimated signal produced by a probe with sequence, s, binding to a homologous genomic sequence, $s_i$, divided by the signal produced by the probe and its perfect-match target sequence that it was designed to interrogate, s', written thus:

$$H_i = S(s,s_i)/S(s,s').$$

To determine $H_i$, in certain embodiments a complex model of signal prediction is employed to calculate the respective contributions from each duplex hybridization event for those targets with significant hybridization under the experimental conditions of the assay. In principle, the signal between each target can be calculated from the two sequences by means of a nearest neighbor model of matching and mismatched nucleotides between the two strands of the duplex.

In alternative embodiments, $H_i$ is calculated using a simplified formula, such as:

$$H_i = (N-m)/(L-m)$$

where N is the number of matching bases within the span of the probe, L is the length of the probe in nucleotides, and m is an offset, chosen to represent the shortest match that can provide a significant signal contribution.

With respect to the proximity weighting function, this function may be a top-hat function with boundaries defined by a CNV that contains the probe. Alternatively, the function may have a more continuous functional form, such as is seen in a Gaussian or Lorentzian form, or any symmetrically decaying exponential. For example, the proximity weighting function may be a Lorentzian function which is centered at the nominal position of the probe, and normalized to a maximal value of 1 at the position of the probe. In yet other embodiments, a hybrid function is employed, such that anywhere within the CNV has a value of unity and decays towards zero with increasing distance from the probe or from the CNV that contains it. The rationale for the generic functional form, rather than the one specific to a CNV, is that not all CNV's have yet been discovered. It is thus more generalizable to probes at any position within the genome where the boundaries of the CNV's are either unknown or too variable to be well-defined. In certain embodiments, a top-hat function is employed for probes within known CNV's and a non-tophat functional form is employed for probes outside known CNV's.

For estimate P, a proximity weighting function, $f(x_i-x_o)$, may be employed, where $x_o$ is the position of the designed target for the probe, $x_i$ is the position of the sequence homologous to the probe. This proximity weighting function $f(x_i-x_o)$ is a function that is maximal and near unity in the vicinity of the CNV or region of interest and is small or zero far from the vicinity of the probe, where this distal position may be on the same chromosome or on another chromosome all-together. In this way, one can estimate the contribution to the probe's signal that comes from genomic sequences close or proximal to its intended target as:

$$P=\Sigma f(x_i-x_o)H_i$$

where the summation is over all homologous sequences $s_i$ for which the product $f(x_i-x_o)H_i$ is significant compared with 1. A product is considered significant compared with 1 if its value is 0.1 or higher, such as 0.2 or higher and including 0.6 or higher.

For determining estimate D, which estimate represents the signal contributions from hybridization events occurring at genomic regions far from the target of interest (as reviewed above, a different weighting function may be employed, for example: $g(x_i-x_o)$. In this case, the weighting function $g(x_i-x_o)$ is minimal or zero near the intended target and is unity far from the target of interest. Indeed, because of the complementary nature of $f(x_i-x_o)$ and $gx_i-x_o)$, it is convenient to define their sum as a constant such that $g(x_i-x_o)+f(x_i-x_o)=1$. One can estimate the contribution to the probe's signal that comes from genomic sequences distal to its intended target as:

$$D=\Sigma g(x_{i-xo})H_i$$

where the summation is over i for all homologous for homologous sequences $s_i$ for which the product $g(x_i-x_o)H_i$ is significant (or detectable). A product is considered significant if its value is 0.001 or higher, such as 0.01 or higher and including 0.05 or higher.

As reviewed above, the invention provides different ways to determine proximity scores for a given candidate probe nucleic acid sequence. For the specific proximity scores described above, the proximity scores approach 1 for probes with large proximal signal contributions and small distal contributions, and approach zero for larger distal contributions. The large distal contributions to signal degrade the specificity of the probe by adding on unwanted background signal from untargeted genomic regions. Where the proximity score that includes the P estimate (i.e., the P-weighted Proximity Score) is employed, one obtains a proximity score that is higher for probes that have multiple copies in or near the region of interest, and hence does not effectively punish these probes relative to another probe that has a single hit in a given CNV interval.

In certain embodiments, the proximity score is one that is defined to have a maximal value of one ("1") for probes unique to the genome, and has a value that approaches zero for probes that have many hits located in genomic regions that are distant from the CNV interval of interest.

Following determination of the proximity score, the candidate probe nucleic acid is evaluated using the proximity score. In evaluating the candidate probe nucleic acid sequence using the proximity score, the proximity score is employed to assess whether a given sequence will be suitable in a physical probe. The assessment may include comparing the proximity score to a reference or threshold value, such that if the score is above the reference value the candidate sequence is considered to be a "satisfactory" sequence that warrants empirical testing and if the score is below the reference value the candidate sequence is considered to a "poor" sequence that does not warrant empirical testing or further consideration, e.g., it should be discarded. For example, where an ideal proximity score is 1 or unity, a reference value may be 0.5 or higher, such as 0.90 or higher and including 0.95 or higher.

In some applications, the proximity score of a probe is compared with that for those in the nearby vicinity to the probe and instead of choosing the probe based on its absolute proximity score, the probe with the highest proximity score will be selected, e.g., as may be identified using a pairwise filtering protocol, such as is described in Published United States Applications No. 2006/0110744 and co-pending application Ser. No. 11/888,059, titled "Methods And Systems For Pairwise Filtering Candidate Probe Nucleic Acid Sequences" and filed on even date herewith; the disclosures of which applications are herein incorporated by reference. In this case, even if a score has a fairly low value it may still be the best in the region of interest. In this case the proximity score provides a means of relative comparison.

In certain embodiments, the proximity score is employed as the sole parameter in an "in silico" evaluation protocol. In yet other embodiments, the proximity score is employed along with one or more additional in silico parameters in an in silico evaluation protocol. Additional parameters of interest include, but are not limited to those in silico parameters described in published United States Patent Application No. 20060110744 titled: "Probe design methods and microarrays for comparative genomic hybridization and location analysis, '" the disclosure of which is herein incorporated by reference. These additional in silico parameters of interest include: restriction cut site analysis, annotation for expression and association with a chromosome of interest, analysis of target structural stability, thermodynamic analysis, pairwise probe selection, determination of a homology signal-to-background score; duplex melting temperature analysis; hairpin structural stability analysis; duplex stability analysis; target specificity analysis; kinetic property analysis, expression analysis; etc.

Evaluation as described above provides a result. The result may take a variety of different formats, where the information content of the result may be simple or complex. For example, the information content of the result may simply be a determination of satisfactory or unsatisfactory determination for a given candidate probe sequence. Alternatively, the information content of the result may be provide additional information, such as the values of the proximity score (and one or more additional in silico parameters) that were determined for the candidate sequence.

The result is then output in some manner, where the outputting results in a physical transformation of matter physical transformation and/or a useful, concrete and tangible result. For example, the result may be made accessible to a user in some manner so as to make it a tangible result. The result may be made accessible in a number of different manners, such as by displaying it to a user, e.g., via a graphical user interface, by recording it onto a physical medium, e.g., a computer readable medium, and human readable medium, e.g., paper, etc. The above embodiments are merely exemplary.

As reviewed above, the above protocol may be employed to evaluate a single candidate sequence, two or more different candidate sequences, e.g., 10 or more, 50 or more, 100 or more, 1000 or more, 10,000 or more, 50,000 or more, 100,000 or more, 1,000,000 or more different sequences.

The above described embodiments provide in silico evaluated candidate probe nucleic acid sequences. Resultant in silico evaluated candidate probe nucleic acids of interest, e.g., those determined in the evaluation to be "satisfactory" may then be further empirically evaluated. In certain. embodiments, empirical evaluation may include synthesizing the physical probes that include the candidate probe nucleic acid sequences of interest and assaying the probes in a hybridization assay. Hybridization assays of interest for these empirical evaluations include contacting an array of candidate probe nucleic acids in the form of surface-bound polynucleotides with a labeled population of nucleic acid acids. Following contact, signals obtained from the surface-bound polynucleotides are compared with a reference, e.g., a previously or concurrently determined control set of values, to evaluate the binding characteristics of one or more of the surface-bound polynucleotides. Examples of empirical assays of interest that may be employed include, but are not limited to: the empirical assays reported in United States Patent Application Nos. 20060110744 and 20070048743; the disclosures of which are herein incorporated by reference.

Figure 1:
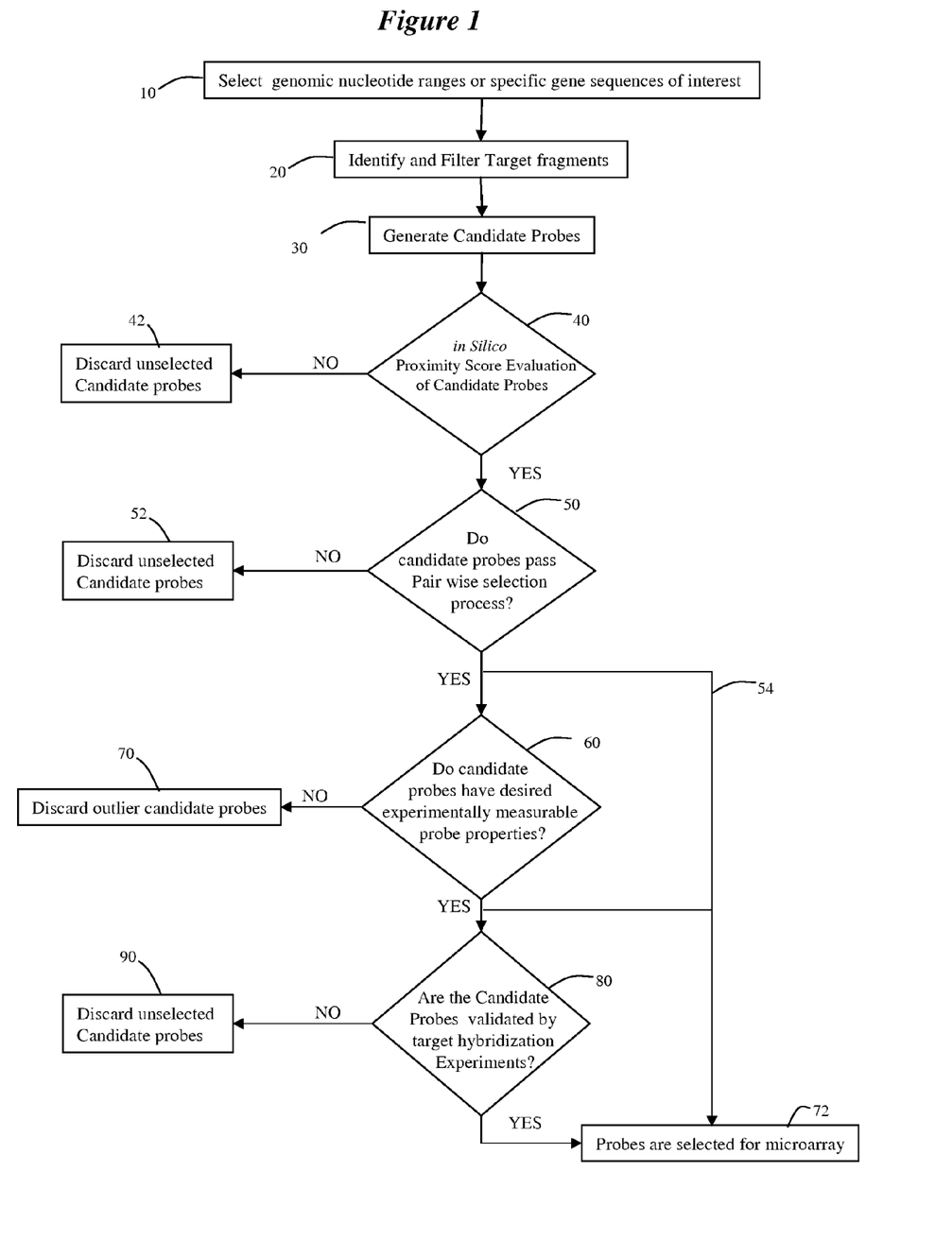
FIG. 1 is a flow chart of a process of probe selection utilizing probe selection parameters for CGH in accordance with the invention.

An example of an embodiment of the invention that includes proximity score based in silico evaluation and an empirical evaluation is depicted in FIG. 1. In FIG. 1, there is shown a flow chart of events that may be carried out in a nucleic acid probe selection method in accordance with the invention. At event 10, a nucleotide sample is selected for probe design for microarray analysis. The nucleotide sample may be a genome or genomic nucleotide range or ranges, such as a chromosome or portion thereof. At event 20, potential target sequences of the nucleotide sample of interest are identified, filtered and reduced to a set of appropriate target sequences for CGH analysis. The potential target sequences are filtered by size, number of repeat-masked bases and/or GC-content. Target sequences are also filtered and reduced in number by eliminating repetitive target sequences in event 20. Another parameter which can be used to filter target sequences is to eliminate potential target sequences which comprise a restriction enzyme cut site. By limiting the size of the set of target sequences, the computational time needed to generate and analyze the candidate probes is decreased.

After determining a set of appropriate target sequences in event 20, candidate probes to the genomic sequence (e.g. chromosome) of interest are generated at event 30 as shown in FIG. 1. Generating a set of candidate probes comprises tiling probes across regions of the target sequences determined in event 20, which enables the candidate probes to be free of repeat-masked section as well as restriction cut sites if desired. The generation of candidate probes may comprise additional filtering and reduction depending on the genomic sequence of interest.

At event 40, the candidate probes are filtered or reduced in total numbers by utilizing indicators or metrics of certain probe properties which assess candidate probe quality in silico, where these properties or parameters that are employed in this step at least include a proximity score, as reviewed above. In silico means those parameters that can be determined without the need to perform any experiments, by using information either calculated de novo or available from public or private databases. Probe parameters utilized to annotate candidate probes may include but are not limited to target specificity, thermodynamic properties, expression and association with genes, homology and also kinetic properties. Candidate probes which do not meet the in silico parameters or indicators for a "good" probe are discarded from the probe selection process at event 42.

Candidate probes which are identified to have certain desirable probe properties in silico, are subjected to a pairwise selection process to filter and reduce the number of potential probes at event 50, where this pairwise selection process may be the process described in published United States Patent Application No. 20060110744; the disclosure of which is herein incorporated by reference. The pairwise filtering evaluates a pair of candidate probes for a probe property or set of property and scores the probes within the pair against each other according to the probe property analyzed. Probes which do not pass the pairwise selection process are not selected and are discarded in event 52. Probes which pass pairwise filtering may require further filtering and can be evaluated experimentally for other desirable probe properties at event 60. In certain embodiments, selecting probes for a CGH based array requires no further filtering or reduction of candidate probes besides those applied by the pairwise and in silico analysis as shown in event 54. As more indicators and metrics for probe performance are identified and adapted for analyzing probe performance in silico, less emphasis is placed on experimental probe results for CGH probe selection.

In the method shown in FIG. 1, candidate probes which meet the pairwise filtering may require further analysis by measuring specific "good" probe indicators/probe properties experimentally at event 60. To obtain a sense of a probe's performance, experiments are completed which measure properties of a probe that can, in the absence of more direct experiments, provide a good indication if a probe will be suitable for a CGH or location analysis array. Such experimentally measurable properties useful in determining a candidate probes performance include but are not limited to; raw signal intensity, reproducibility of signal intensity, dye bias, and susceptibility of non-specific binding.

Candidate probes which do not meet the experimentally measurable probe parameters are discarded/unselected in event 70, while the remaining candidate probes which meet the probe parameter standards in event 60 may be utilized for CGH arrays, event 72 or be subjected to further filtering by completing probe validation experiments at event 80. The order in which experimentally measurable probe parameters are applied to candidate probes may vary depending on the genomic sequence of interest.

At event 80, candidate probes are placed on an array and subjected to a plurality of target sets/samples. The probes are evaluated and scored by assessing a plurality of probe properties over numerous target sets. The candidate probes are evaluated in event 80 for adequate signal response as well as reproducibility across target sets. The candidate probes which obtain a high validation score from the validation experiments are suitable for use on a CGH array, event 72, while candidate probes with deficient or poor validation scores are not selected in event 90. Empirical assays to which the probes may be subjected in step 60 include those described in United States Patent Application Nos. 20060110744 and 20070048743; the disclosures of which are herein incorporated by reference.

Depending on the space available on the array chip, more or fewer probe parameters can be implemented and/or the thresholds and cut-offs of probe parameters may be adjusted as needed. Candidate probes may be prioritized, for example gene-by-gene, region-by region, or strictly filtered on validation scores. Also, annotation of probes for position, gene association and expression may also be utilized to finalize the probe selection for a CGH or location array.

The methods described above provide surface-bound polynucleotides with desirable binding characteristics. Once such surface-bound polynucleotides with desirable binding characteristics, i.e., "validated" surface-bound polynucleotides, have been identified, they may be used to fabricate an array. Accordingly, the invention provides a method of producing an array. In general, the method involves identifying a surface-bound polynucleotide with desirable binding characteristic, and fabricating an array containing that polynucleotide. A subject array may contain 1, 2, 3, more than about 5, more than about 10, more than about 20, more than about 50, more than about 100, more than about 200, more than about 500, more than about 1000, more than about 2000, more than about 5000 or more, usually up to about 10,000 or more, "validated" surface-bound polynucleotides.

Arrays can be fabricated using any means, including drop deposition from pulse jets or from fluid-filled tips, etc, or using photolithographic means. Either polynucleotide precursor units (such as nucleotide monomers), in the case of in situ fabrication, or previously synthesized polynucleotides (e.g., oligonucleotides, amplified cDNAs or isolated BAC, bacteriophage and plasmid clones, and the like) can be deposited. Such methods are described in detail in, for example U.S. Pat. Nos. 6,242,266, 6,232,072, 6,180,351, 6,171,797, 6,323,043, etc.

Array platforms of interest include, but are not limited to: U.S. patents of interest include: U.S. Pat. Nos. 6,465,182; 6,335,167; 6,251,601; 6,210,878; 6,197,501; 6,159,685; 5,965,362; 5,830,645; 5,665,549; 5,447,841 and 5,348,855. Also of interest are published United States Application Serial Nos. 20020006622; 20040241658 and 20040191813, as well as published PCT application WO 99/23256.

The resultant arrays find use in, among other applications, identifying surface-bound polynucleotides suitable for use in CGH assays, e.g., any application in which one wishes to compare the copy number of nucleic acid sequences found in two or more genomic samples. Once identified, surface-bound polynucleotides suitable for use in CGH assays may be used to make a CGH array, e.g., as described above. Such a CGH array may be used in CGH assays to obtain high quality, reliable, data that is free from the artifacts (e.g. compression of observed ratios due to crosshybridization of surface-bound polynucleotides with non-target sequences) commonly obtained using CGH arrays containing surface-bound polynucleotides identified using other methods. Accordingly, the subject methods find use in making CGH arrays.

One type of application in which the subject CGH arrays find use is the quantitative comparison of copy number of one nucleic acid sequence in a first collection of nucleic acid molecules relative to the copy number of the same sequence in a second collection.

As such, the present invention may be used in methods of comparing abnormal nucleic acid copy number and mapping of chromosomal abnormalities associated with disease. In many embodiments, the subject methods are employed in applications that use polynucleotides immobilized on a solid support, to which differentially labeled nucleic acids produced as described above are hybridized. Analysis of processed results of the described hybridization experiments provides information about the relative copy number of nucleic acid domains, e.g. genes, in genomes.

Such applications compare the copy numbers of sequences capable of binding to the target elements. Variations in copy number detectable by the methods of the invention may arise in different ways. For example, copy number may be altered as a result of amplification or deletion of a chromosomal region, e.g. as commonly occurs in cancer.

Representative applications in which the subject methods find use are further described in U.S. Pat. Nos. 6,335,167; 6,197,501; 5,830,645; and 5,665,549; the disclosures of which are herein incorporated by reference.

In particular embodiments, CGH arrays containing surface-bound oligonucleotides, i.e., oligonucleotides of 10 to 100 nucleotides and up to 200 nucleotides in length, are employed.

Generally, comparative genome hybridization methods comprise the following major steps: (1) immobilization of polynucleotides on a solid support; (2) pre-hybridization treatment to increase accessibility of support-bound polynucleotides and to reduce nonspecific binding; (3) hybridization of a mixture of labeled nucleic acids to the surface-bound nucleic acids, typically under high stringency conditions; (4) post-hybridization washes to remove nucleic acid fragments not bound to the solid support polynucleotides; and (5) detection of the hybridized labeled nucleic acids. The reagents used in each of these steps and their conditions for use vary depending on the particular application.

As indicated above, hybridization is carried out under suitable hybridization conditions, which may vary in stringency as desired. In certain embodiments, highly stringent hybridization conditions may be employed. The term "high stringent hybridization conditions" as used herein refers to conditions that are compatible to produce nucleic acid binding complexes on an array surface between complementary binding members, i.e., between the surface-bound polynucleotides and complementary labeled nucleic acids in a sample. Representative high stringency assay conditions that may be employed in these embodiments are provided above.

The above hybridization step may include agitation of the immobilized polynucleotides and the sample of labeled nucleic acids, where the agitation may be accomplished using any convenient protocol, e.g., shaking, rotating, spinning, and the like.

Following hybridization, the array-surface bound polynucleotides are typically washed to remove unbound labeled nucleic acids. Washing may be performed using any convenient washing protocol, where the washing conditions are typically stringent, as described above.

Following hybridization and washing, as described above, the hybridization of the labeled nucleic acids to the targets is then detected using standard techniques so that the surface of immobilized targets, e.g., the array, is read. Reading of the resultant hybridized array may be accomplished by illuminating the array and reading the location and intensity of resulting fluorescence at each feature of the array to detect any binding complexes on the surface of the array. For example, a scanner may be used for this purpose, which is similar to the AGILENT MICROARRAY SCANNER available from Agilent Technologies, Palo Alto, Calif. Other suitable devices and methods are described in U.S. Pat. No. 6,756,202 and 6,406,849, which references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of nucleic acids, and are suitable for some embodiments.

Results from the reading or evaluating may be raw results (such as fluorescence intensity readings for each feature in one or more color channels) or may be processed results (such as those obtained by subtracting a background measurement, or by rejecting a reading for a feature which is below a predetermined threshold, normalizing the results, and/or forming conclusions based on the pattern read from the array (such as whether or not a particular target sequence may have been present in the sample, or whether or not a pattern indicates a particular condition of an organism from which the sample came).

In certain embodiments, the subject methods include a step of transmitting data or results from at least one of the detecting and deriving steps, also referred to herein as evaluating, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

The invention also provides a variety of computer-related embodiments. Specifically, the data analysis methods described in the previous section may be performed using a computer. Accordingly, the invention provides a computer-based system for analyzing data produced using the above methods in order to screen and identify surface-bound polynucleotides with desirable binding characteristics.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

In certain embodiments, the computer readable medium is a medium carrying one or more sequences of instructions for evaluating a candidate probe CGH nucleic acid sequence, wherein execution of one or more sequences of instructions by one or more processors causes the one or more processors to perform the steps of: (a) determining a proximity score for a candidate CGH probe nucleic acid sequence for a target sequence of a copy number variation (CNV) of a genome; (b) evaluating said candidate CGH probe nucleic acid sequence using said proximity score to obtain a result; and (c) outputting said result.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

Aspects of the invention further includes sytems, e.g., computer based systems, that are configured to evaluate a candidate probe nucleic acid sequence. A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Embodiments of the subject systems include the following components: (a) a communications module for facilitating information transfer between the system and one or more users, e.g., via a user computer, as described below; and (b) a processing module for performing one or more tasks involved in the probe qualification methods of the invention. In certain embodiments, the subject systems may be viewed as being the physical embodiment of a web portal, where the term "web portal" refers to a web site or service, e.g., as may be viewed in the form of a web page, that offers a broad array of resources and services to users via an electronic communication element, e.g., via the Internet.

Figure 2:
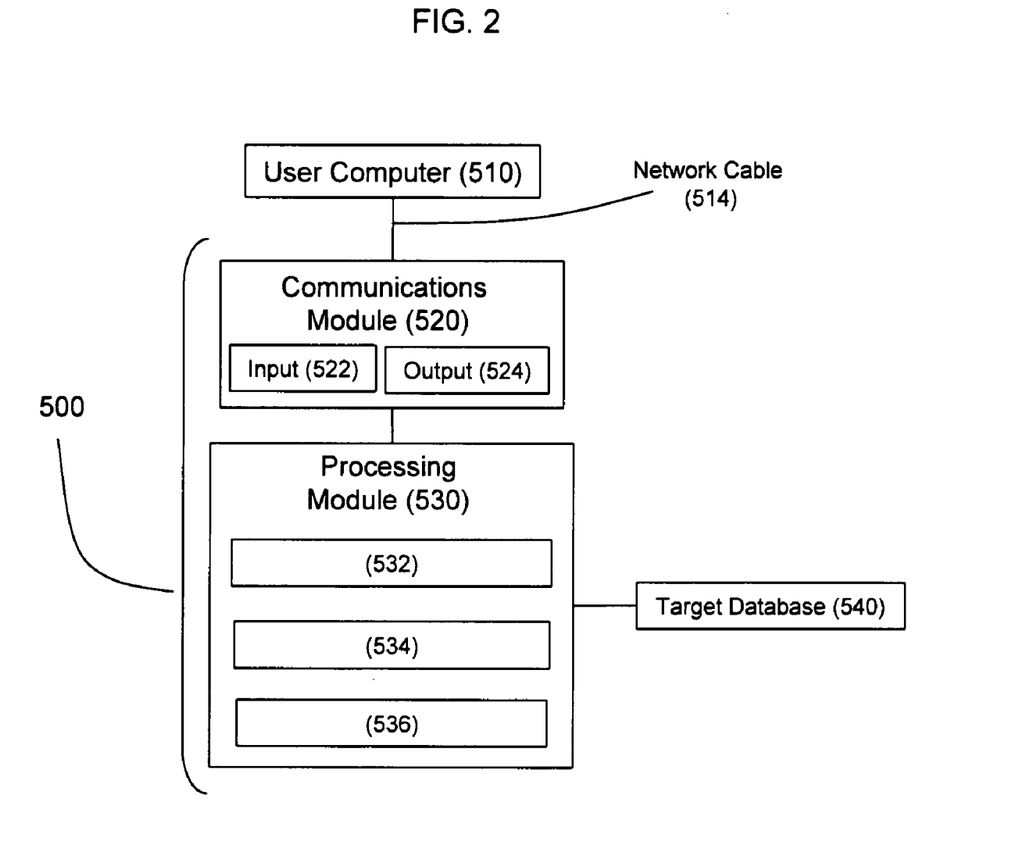
FIG. 2 schematically illustrates a system according to an embodiment of the invention.

FIG. 2 provides a view of a representative probe qualification system according to an embodiment of the subject invention. In FIG. 2, system 500 includes communications module 520 and processing module 530, where each module may be present on the same or different platforms, e.g., servers, as described above.

The communications module includes the input manager 522 and output manager 524 functional elements. Input manager 522 receives information from a user e.g., over the Internet. Input manager 522 processes and forwards this information to the processing module 530. These functions are implemented using any convenient method or technique. Another of the functional elements of communications module 520 is output manager 524. Output manager 524 provides information assembled by processing module 530 to a user, e.g., over the Internet. The presentation of data by the output manager may be implemented in accordance with any convenient methods or techniques. As some examples, data may include SQL, HTML or XML documents, email or other files, or data in other forms. The data may include Internet URL addresses so that a user may retrieve additional SQL, HTML, XML, or other documents or data from remote sources.

The communications module 520 may be operatively connected to a user computer 510, which provides a vehicle for a user to interact with the system 500. User computer 510, shown in FIG. 2, may be a computing device specially designed and configured to support and execute any of a multitude of different applications. Computer 510 also may be any of a variety of types of general-purpose computers such as a personal computer, network server, workstation, or other computer platform now or later developed. Computer 510 may include components such as a processor, an operating system, a graphical user interface (GUI) controller, a system memory, memory storage devices, and input-output controllers. There are many possible configurations of the components of computer 510 and some components are not listed above, such as cache memory, a data backup unit, and many other devices.

In certain embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In certain embodiments, a user employs the user computer to enter information into and retrieve information from the system. As shown in FIG. 2, computer 510 is coupled via network cable 514 to the system 500. Additional computers of other users and/or administrators of the system in a local or wide-area network including an Intranet, the Internet, or any other network may also be coupled to system 500 via cable 514. It will be understood that cable 514 is merely representative of any type of network connectivity, which may involve cables, transmitters, relay stations, network servers, wireless communication devices, and many other components not shown suitable for the purpose. Via user computer 510, a user may operate a web browser served by a user-side Internet client to communicate via Internet with system 500. System 500 may similarly be in communication over Internet with other users, networks of users, and/or system administrators, as desired.

As reviewed above, the systems include various functional elements that carry out specific tasks on the platforms in response to information introduced into the system by one or more users. In FIG. 2, elements 532, 534 and 536 represent three different functional elements of processing module 530. While three different functional elements are shown, it is noted that the number of functional elements may be more or less, depending on the particular embodiment of the invention. Functional elements that may be carried out by the processing module including a functional element configured to evaluate a candidate nucleic acid probe sequence according to an embodiment of the invention, e.g., as described above.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention.

It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   (a) providing a candidate CGH probe nucleic acid sequence complementary to a target sequence of a copy number variation (CNV) in a genome;
   (b) calculating a proximity score for said candidate CGH probe nucleic acid sequence, wherein said proximity score is determined by proximity to said target sequence of one or more sequences homologous to said target sequence;
   wherein said proximity score is an indicator of suitability of said candidate CGH probe nucleic acid sequence for use in detecting said CNV,
   wherein said method is implemented on a specifically programmed computer.

2. The method according to claim 1, wherein said proximity score is determined from an estimate (D) of signal contributions from hybridization of said candidate CGH probe nucleic acid sequence to said one or more sequences distal to said target sequence.

3. The method according to claim 2, wherein said proximity score is determined using the formula:

$$\text{Proximity score}=1/(1+D).$$

4. The method according to claim 1, wherein said proximity score is determined from an estimate (D) of signal contributions from hybridization of said candidate CGH probe nucleic acid sequence to said one or more sequences distal to said target sequence and also from an estimate (P) of signal contributions from hybridization of said candidate CGH probe to said one or more sequences at least proximal to said target sequence.

5. The method according to claim 4, wherein said hybridization of said candidate CGH probe nucleic acid sequence to said one or more sequences at least proximal to said target sequence comprises hybridization occurring at said target sequence and proximal to said target sequence.

6. The method according to claim 5, wherein said proximity score is determined using the formula:

Proximity score=$P/(P+D)$.

7. The method according to claim 1, wherein said proximity score is determined using a proximity weighting function.

8. The method according to claim 7, wherein said proximity weighting function is a "top-hat" function.

9. The method according to claim 7, wherein said proximity weighting function is a continuous function.

10. The method according to claim 9, wherein said proximity weighting function is a Lorentzian function.

11. The method according to claim 1, wherein said outputting comprises recording said result to a physical medium.

12. The method according to claim 1, wherein at least two different candidate CGH probe nucleic acid sequences of differing sequence are provided in step (a), and step (b) is carried out on said at least two different candidate CGH probe nucleic acid sequences.

13. The method according to claim 1, wherein said method further comprises synthesizing a probe nucleic acid having a sequence of said candidate CGH probe nucleic acid sequence.

14. The method according to claim 13, wherein said method further comprises assaying said probe nucleic acid in a hybridization assay.

15. The method according to claim 1, wherein said method further comprises fabricating a nucleic acid array that comprises said candidate CGH probe nucleic acid sequence.

16. The method according to claim 15, wherein said method further comprises contacting said nucleic acid array with a genomic sample.

17. A computer readable storage medium carrying one or more sequences of instructions for evaluating a candidate probe CGH nucleic acid sequence, wherein execution of said one or more sequences of instructions by one or more processors causes the one or more processors to perform the step of:
  calculating a proximity score for a candidate CGH probe nucleic acid sequence complementary to a target sequence of a copy number variation (CNV) in a genome, wherein said proximity score is determined by proximity to said target sequence of one or more sequences homologous to said target sequence; wherein said proximity score is an indicator of suitability of said candidate CGH probe nucleic acid sequence for use in detecting said CNV.

18. A computer-based system for evaluating a candidate probe CGH nucleic acid sequence, said computer-based system comprising:
  (a) a communication module comprising an input manager for receiving input from a user and an output manager for communicating output to a user;
  (b) a processor comprising a candidate probe CGH nucleic acid sequence manager program that causes the processor to:
  calculate a proximity score for a candidate CGH probe nucleic acid sequence complementary to a target sequence of a copy number variation (CNV) in a genome, wherein said proximity score is determined by proximity to said target sequence of one or more sequences homologous to said target sequence and wherein said proximity score is an indicator of suitability of said candidate CGH probe nucleic acid sequence for use in detecting said CNV.

* * * * *